US012427230B2

(12) United States Patent
Kim et al.

(10) Patent No.: US 12,427,230 B2
(45) Date of Patent: Sep. 30, 2025

(54) HUMAN NASAL TURBINATE-DERIVED MESENCHYMAL STEM CELL-BASED, 3D BIOPRINTED CONSTRUCT, AND USE THEREOF

(71) Applicant: CATHOLIC UNIVERSITY INDUSTRY ACADEMIC COOPERATION FOUNDATION, Seoul (KR)

(72) Inventors: Sung Won Kim, Seoul (KR); Jung Yeon Lim, Seoul (KR); Sun Hwa Park, Seoul (KR); Byeong Gon Yoon, Suwon-si (KR); Dong-Woo Cho, Seoul (KR); Jinah Jang, Pohang-si (KR); Seok Won Kim, Seoul (KR)

(73) Assignee: CATHOLIC UNIVERSITY INDUSTRY ACADEMIC COOPERATION FOUNDATION, Seoul (KR)

( * ) Notice: Subject to any disclaimer, the term of this patent is extended or adjusted under 35 U.S.C. 154(b) by 0 days.

(21) Appl. No.: 18/583,237

(22) Filed: Feb. 21, 2024

(65) Prior Publication Data

US 2024/0189482 A1 Jun. 13, 2024

Related U.S. Application Data

(62) Division of application No. 16/609,887, filed as application No. PCT/KR2018/005068 on May 2, 2018, now Pat. No. 11,938,247.

(30) Foreign Application Priority Data

May 2, 2017 (KR) .................. 10-2017-0056451
Apr. 30, 2018 (KR) .................. 10-2018-0050195

(51) Int. Cl.
| | | |
|---|---|---|
| *A61L 27/38* | (2006.01) | |
| *A61L 27/20* | (2006.01) | |
| *A61L 27/24* | (2006.01) | |
| *A61L 27/52* | (2006.01) | |
| *A61L 27/54* | (2006.01) | |

(52) U.S. Cl.
CPC .......... *A61L 27/3834* (2013.01); *A61L 27/20* (2013.01); *A61L 27/24* (2013.01); *A61L 27/52* (2013.01); *A61L 27/54* (2013.01); *A61L 2400/06* (2013.01)

(58) Field of Classification Search
None
See application file for complete search history.

(56) References Cited

U.S. PATENT DOCUMENTS

2009/0263849 A1   10/2009   Sun et al.

FOREIGN PATENT DOCUMENTS

| KR | 10-2011-0106235 A | 9/2011 |
| KR | 20110106235 A * | 9/2011 |
| KR | 10-1327076 B1 | 11/2013 |
| WO | 2014/168585 A1 | 10/2014 |
| WO | 2015/173020 A1 | 11/2015 |

OTHER PUBLICATIONS

Jang et al., "A MSCs-laden polycaprolactone/collagen scaffold for bone tissue regeneration", RSC Adv., (2016), vol. 6, pp. 6259-6265 (Year: 2016).*
Kang et al., A 3D bioprinting system to produce human-scale tissue constructs with structural integrity, Feb. 15, 2016, Nature Biotechnology, p. 1-11 (Year: 2016).*
Jang et al., "A MSCs-laden polycaprolactone/collagen scaffold for bone tissue regeneration", RSC Adv., (2016), vol. 6, pp. 6259-6265.

\* cited by examiner

*Primary Examiner* — Erin E Hirt
*Assistant Examiner* — Ali S Saeed
(74) *Attorney, Agent, or Firm* — Vorys, Sater, Seymour and Pease LLP; Mih Suhn Koh

(57) ABSTRACT

Provided are a method for fabricating a human nasal turbinate-derived mesenchymal stem cell-based 3D bioprinted construct, and a use thereof, wherein the human nasal turbinate-derived mesenchymal stem cell-based, 3D bioprinted construct is advantageous over conventional mesenchymal stem cell-based, 3D bioprinted constructs in that the former can survive and proliferate stably in vitro and/or in vivo and shows high osteogenic differentiation ability as well, therefore is expected to make a great contribution to the practical use of cellular therapeutic agents.

4 Claims, 16 Drawing Sheets

HUMAN NASAL TURBINATE-DERIVED MESENCHYMAL STEM CELL-BASED, 3D BIOPRINTED CONSTRUCT, AND USE THEREOF

CROSS-REFERENCE TO RELATED APPLICATION

This application is a divisional of U.S. patent application Ser. No. 16/609,887, filed on Oct. 31, 2019, which was a 371 of PCT/KR2018/005068, filed May 2, 2018, which claims the benefit of priority from Korean Patent Application No. 10-2017-0056451, filed May 2, 2017 and Korean Patent Application No. 10-2018-0050195, filed Apr. 30, 2018, the contents of each of which are incorporated herein by reference in its entirety.

STATEMENT REGARDING GOVERNMENT RIGHTS

The present invention was undertaken with the support of 1) the Korea Health Industry Development Institute (KHIDI) No. HI13C3228 funded by the Ministry of Health and Welfare, and 2) the Bio & Medical Technology Development Program of the National Research Foundation (NRF) No. NRF-2019M3E5D5064110 grant funded by the Korean government (MSIT).

TECHNICAL FIELD

The present invention relates to a method for fabricating 3D bioprinted construct based a human nasal turbinate-derived mesenchymal stem cells, and a use of the 3D bioprinted construct.

BACKGROUND ART

Tissue engineering is a base technology in the bio organ/new drug field, which is one of the ten next-generation growth-driven industries, and studies on regenerative medicine based on the 3D printing technology have been frequently conducted. However, by implanting conventional biocompatible customized 3D printed constructs with a customized scaffold concept that expects the maintenance of a simple human body outer skeleton and the recruitment of in vivo residual structural cells after the 3D printed construct is implanted, it is impossible to regenerate reproducible consistent functional human body tissues and organs. Therefore, a 3D bioprinted technology using stem cells that can be differentiated into various tissues based on a 3D printed technology for effective regeneration of human tissues and organs has drawn attention as a new growth engine for the future, and there is a need for studies on the development of a 3D printing-based stem cellular therapeutic agent as a new research area that leads the concept of a next-generation stem cellular therapeutic agent.

Mesenchymal stem cells may be obtained from bone marrow, sucked adipose tissue, cord blood, the umbilical cord, and the like which are adult tissues, and have a fibroblast form. Since the cells can proliferate without limitation in a test tube, and can be differentiated into various types of important cell lineages such as fat, osteocytes, chondrocytes, cardiac muscle cells, and nerve cells unlike blood stem cells, many studies have been conducted in the tissue engineering and regenerative medicine fields (KR10-1327076).

Meanwhile, an operation for the acquirement of the mesenchymal stem cells may be accompanied by severe pain, or may need general or spinal anesthesia, and has brought problems in that the amount of mesenchymal stem cells acquired is very small, a lot of time and money are required while a clinically sufficient amount thereof is cultured, and a risk of contamination and cell loss is high.

Thus, the present inventors have tried to develop, as an alternative for overcoming these problems, a method capable of fabricating an effective and stable stem cell 3D construct using a human nasal turbinate-derived mesenchymal stem cell-based 3D bioprinted technology that is more highly accessible than a conventional mesenchymal stem cell donor.

DISCLOSURE

Technical Problem

An object of the present invention is to provide a method for fabricating a human nasal turbinate-derived mesenchymal stem cell-based 3D bioprinted construct.

Further, another object of the present invention is to provide a cellular therapeutic agent including, as an active ingredient, a human nasal turbinate-derived mesenchymal stem cell-based 3D bioprinted construct.

However, the technical problems which the present invention intends to solve are not limited to the technical problems which have been mentioned above, and other technical problems which have not been mentioned will be clearly understood by a person with ordinary skill in the art to which the present invention pertains from the following description.

Technical Solution

In order to achieve the objects of the present invention as described above, the present invention provides a method for fabricating a human nasal turbinate-derived mesenchymal stem cell-based 3D bioprinted stem cell construct, the method including steps of:
(a) isolating mesenchymal stem cells from a nasal turbinate tissue collected during the process of surgically removing the human nasal turbinate tissue;
(b) fabricating a bioink by encapsulating the isolated mesenchymal stem cells in a hydrogel; and
(c) fabricating a 3D bioprinted stem cell construct by a micro-extrusion method by mixing the bioink with polycaprolactone (PCL).

As an embodiment of the present invention, the method may further include a step of stabilizing the 3D bioprinted stem cell construct fabricated in step (c) in a stabilization culture broth.

As another embodiment of the present invention, the hydrogel in step (b) may be collagen or alginate.

Further, the present invention provides a cellular therapeutic agent including, as an active ingredient, the human nasal turbinate-derived mesenchymal stem cell-based 3D bioprinted stem cell construct fabricated by the method.

As an embodiment of the present invention, the cellular therapeutic agent may be a cellular therapeutic agent for treating a bone defect, but is not limited thereto.

Further, the present invention provides a method for preventing or treating a disease, comprising a step of administering to subject, a cellular therapeutic agent comprising, as an active ingredient, the human nasal turbinate-derived mesenchymal stem cell-based 3D bioprinted stem cell construct.

Advantageous Effects

The present invention relates to a method for fabricating a human nasal turbinate-derived mesenchymal stem cell-based 3D bioprinted construct, and a use thereof. Conventional mesenchymal stem cells are accompanied by severe pain in the acquirement procedure thereof, have a limitation in the time of acquirement, and require a lot of time and money and have a high risk of being contaminated during the cultivation thereof in a sufficient quantity. In contrast, human nasal turbinate-derived mesenchymal stem cells have the advantages of having a low likelihood of surgery for the acquirement thereof and a capacity of being acquired in a sufficient amount anytime. In addition, a human nasal turbinate-derived mesenchymal stem cell-based, 3D bioprinted construct is advantageous over conventional mesenchymal stem cell-based, 3D bioprinted constructs in that the former can survive and proliferate stably in vitro and/or in vivo and shows a high osteogenic differentiation ability, a bone defect regeneration ability, and a survival and differentiation ability in bone defect sites as well.

Thanks to the advantages, human nasal turbinate-derived mesenchymal stem cells allow the easy fabrication of 3D bioprinted constructs which are thus expected to make a great contribution to the practical use of cellular therapeutic agents. In addition, the 3D bioprinted construct fabricated by the method of the present invention has the same genetic origin as the used human nasal turbinate-derived mesenchymal stem cells, and thus enables an immuno-compatible cellular therapeutic agent tailored to each individual to be provided.

MODES OF THE INVENTION

Figure 1:
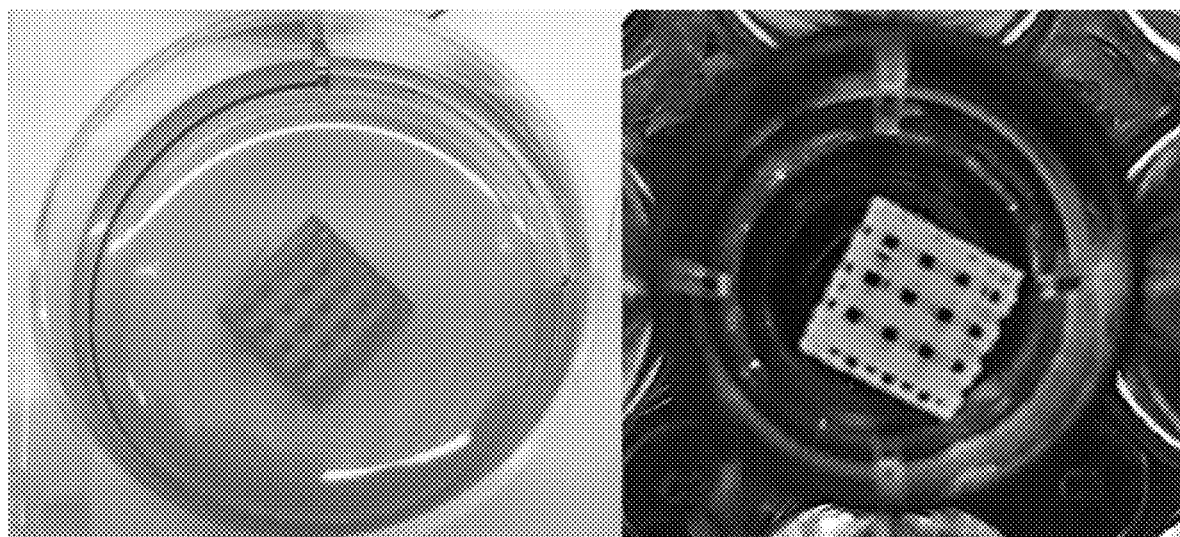
FIG. 1 is a view illustrating a 3D bioprinted construct.
Figure 2A:
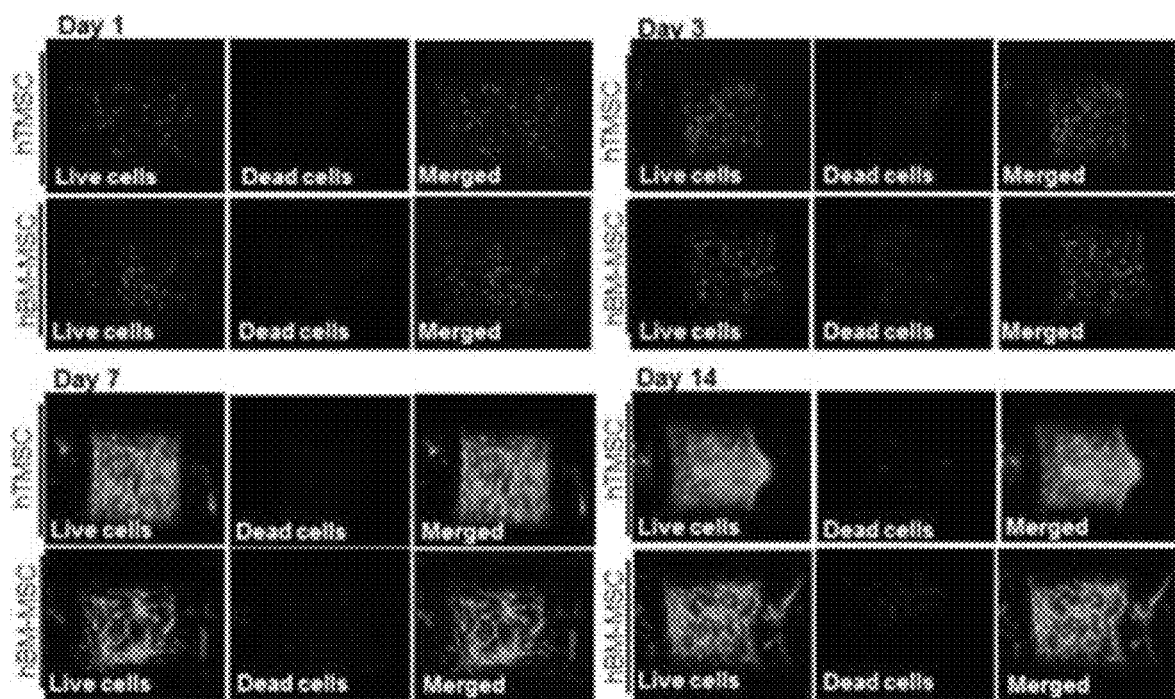
FIGS. 2A and 2C are views illustrating the in vitro stability of cells of a 3D bioprinted construct.
Figure 2B:
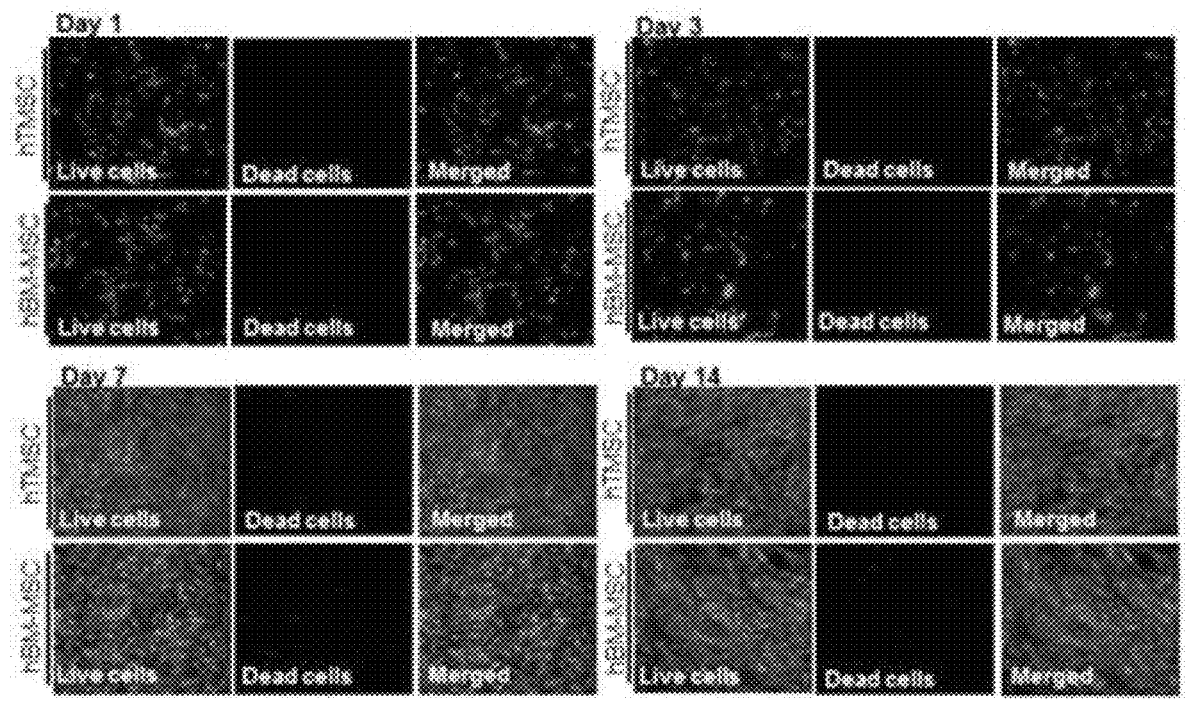
FIGS. 2B and 2D are views illustrating the change in proliferation ability of cells of a 3D bioprinted construct in vitro.
Figure 2C:
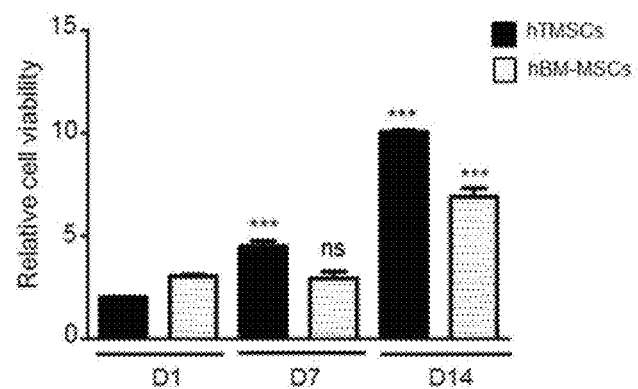
Figure 2D:
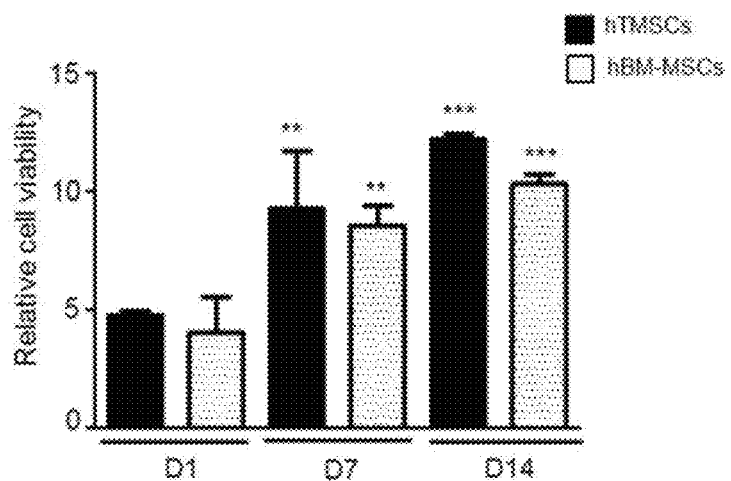

The present inventors found a method for fabricating a 3D bioprinted construct, which is excellent in cell stability, proliferation ability, osteogenic differentiation ability, bone defect regeneration ability, and survival and differentiation ability in bone defect sites from human nasal turbinate-derived mesenchymal stem cells, and thus, the present invention provides a method for fabricating a human nasal turbinate-derived mesenchymal stem cell-based 3D bioprinted construct, and a cellular therapeutic agent including a 3D bioprinted construct fabricated by the method.

Hereinafter, the present invention will be described in detail.

The present invention provides a method for fabricating a human nasal turbinate-derived mesenchymal stem cell-based 3D bioprinted construct, the method including steps of:

(a) isolating mesenchymal stem cells from a nasal turbinate tissue collected during the process of surgically removing the human nasal turbinate tissue;

(b) fabricating a bioink by encapsulating the isolated mesenchymal stem cells in a hydrogel; and (c) fabricating a 3D bioprinted stem cell tissue by a micro-extrusion method by mixing the bio-ink with polycaprolactone (PCL).

In the present invention, the method may further include a step of stabilizing the 3D bioprinted stem cell construct fabricated in step (c) in a stabilization culture broth.

In an example of the present invention, the hydrogel may be collagen or alginate, preferably collagen, but is not limited thereto (see Example 1).

In another example of the present invention, as a result of measuring the in vitro cell stability, proliferation ability, and osteogenic differentiation ability of a 3D bioprinted construct, it was confirmed that the in vitro cell stability, proliferation ability, and osteogenic differentiation ability of a 3D bioprinted construct using human nasal turbinate-derived mesenchymal stem cells were higher than those of a 3D bioprinted construct using bone marrow-derived mesenchymal stem cells (see Examples 2 and 3).

In still another example of the present invention, as a result of measuring the in vivo cell attachment ability and osteogenesis-related changes of a 3D bioprinted construct, it was confirmed that cells are better attached in vivo and better differentiated into osteocytes in a 3D bioprinted construct using human nasal turbinate-derived mesenchymal stem cells than in a 3D bioprinted construct using bone marrow-derived mesenchymal stem cells (see Example 4).

In yet another example of the present invention, as a result of measuring the in vivo bone defect regeneration ability of a 3D bioprinted construct, it was confirmed that osteoregeneration occurred more remarkably in a 3D bioprinted construct using human nasal turbinate-derived mesenchymal stem cells than in a 3D bioprinted construct using bone marrow-derived mesenchymal stem cells (see Example 5).

In yet another example of the present invention, as a result of measuring the in vivo survival and differentiation ability in bone defect sites in a 3D bioprinted construct, it was confirmed that the possibility of in vivo osteogenic differentiation and calcium accumulation was much higher in a 3D bioprinted construct using human nasal turbinate-derived mesenchymal stem cells than in a 3D bioprinted construct using bone marrow-derived mesenchymal stem cells (see Example 6).

As used herein, the term "stem cell" refers to, as a cell that forms a basis of a cell or tissue that constitutes an individual, a cell that may be repeatedly divided to achieve self-renewal and has a multi-differentiation potency to be differentiated into a cell having a specific function according to an environment. Stem cells are generated in all tissues during the fetal development process, and are found in some tissues where cells are actively replaced, such as bone marrow and epithelial tissues, even in adults. Stem cells are classified into totipotent stem cells that are formed when fertilized eggs begin their first division, pluripotent stem cells that are located in the inner cell mass of a blastocyst that is created by the continuous division of these cells, and multipotent stem cells present in mature tissues and organs. In this case, multipotent stem cells are cells that can be differentiated into only cells specific for tissues and organs in which these cells are included, and are involved in not only the growth and development of each tissue and organ in the fetal period, neonatal period, and adult period, but also functions of maintaining homeostasis of a living tissue and inducing regeneration during tissue damage. Such tissue-specific multipotent cells are collectively referred to as adult stem cells.

Mesenchymal stem cells classified into adult stem cells are cells that have drawn attention as a material for regenerative medicine, may be collected from tissues such as bone marrow, cord blood, and the umbilical cord, and have the ability to be differentiated into cells constituting various human body tissues such as adipose tissue cells, osteocytes, chondrocytes, nerve cells, and cardiac muscle cells unlike blood stem cells. In the present invention, mesenchymal stem cells isolated from a human nasal turbinate tissue were used.

Further, the present invention provides a cellular therapeutic agent including, as an active ingredient, the human nasal turbinate-derived mesenchymal stem cell-based 3D bioprinted construct fabricated by the method.

As an embodiment of the present invention, the cellular therapeutic agent may be a cellular therapeutic agent for treating a bone defect, but is not limited thereto.

As used herein, the term "cellular therapeutic agent" refers to a drug used for the purpose of treatment, diagnosis, and prevention, using a cell or tissue prepared through isolation from a human, culture and specific operations (US FDA regulation), and specifically, it refers to a drug in which these cells are used for the purpose of treatment, diagnosis, and prevention through a series of actions of in vitro multiplying and sorting living autologous, allogeneic and xenogeneic cells or changing the biological characteristics of cells by other methods in order to recover the functions of cells or tissues.

A preferred dosage of the cellular therapeutic agent of the present invention varies depending on the condition and body weight of an individual, the degree of a disease, the form of drug, the administration route, and the duration, but may be appropriately selected by a person skilled in the art. The administration may be performed once daily or performed several times, and the dosage does not limit the scope of the present invention in any way.

Hereinafter, preferred examples for helping the understanding of the present invention will be suggested. However, the following examples are provided only to more easily understand the present invention, and the contents of the present invention are not limited by the following examples.

MODE FOR INVENTION

Example 1. Fabrication of Human Nasal Turbinate-Derived Mesenchymal Stem Cell-Based 3D Bioprinted Construct The nasal turbinate tissue used in the present study was obtained during the process of surgically removing the nasal turbinate, and was used with the consent of a patient before surgery. Immediately after the nasal turbinate tissue was collected, fibroblasts were isolated by washing the tissue 3 to 5 times with physiological saline including gentamycin (Kukje Pharm Ind. Co., Ltd., Seongnam, Korea).

In order to isolate the human nasal turbinate-derived mesenchymal stem cells, the surgically removed nasal turbinate tissue was stored at 4° C., and the tissue was washed three times with an antibiotic-antifungal solution (Gibco, Gaithersburg, MD). The tissue was again washed twice with neutral phosphate buffered saline (PBS), and then finely cut into a size of 1 mm$^3$ using surgical scissors.

The cut tissue was placed on a 100-mm culture dish, covered with a sterilized slide glass, adhered to the culture dish, and cultured in an incubator under an environment of 37° C. and 5% $CO_2$ after adding a Dulbecco's Modified Eagle's Media (DMEM) supplemented with 10% fetal bovine serum (FBS) thereto. After 2 to 3 weeks of culture, the slide glass was removed, cells floating in the culture broth were washed and discarded, human nasal turbinate-derived mesenchymal stem cells attached to the bottom of the culture dish were detached from the bottom using trypsin, and cells subcultured up to passage 3 were used.

A 2% bio-ink was fabricated by mixing cells obtained by the culture method with 3% collagen, and a 3D printed stem cell construct was fabricated by a micro-extrusion method together with polycaprolactone (PCL) using a multihead dispenser. The 3D printing conditions are as follows.

PCL condition: nozzle 25N (inner diameter 0.25 mm, outer diameter 0.45 mm)
Feed rate: 400 mm/min
Injection pressure: 500 kPa
Temperature: 80° C.
Conditions for cell encapsulated in collagen:
Nozzle: 26 G (inner diameter 0.25 mm, outer diameter 0.46 mm)
Feed rate: 80 mm/min
Injection rate: 0.04 mm/s
Temperature: 15 to 20° ° C.

As a result, the 3D bioprinted construct in FIG. 1 was fabricated.

Example 2. Analysis of In Vitro Stability and Proliferation Ability of 3D Bioprinted Construct After human nasal turbinate-derived mesenchymal stem cells and bone marrow-based stem cells were put into a culture broth supplemented with 10% FBS and a culture broth supplemented with 20% FBS, respectively, and cultured in vitro for 1, 7, and 14 days by fabricating a 3D bioprinted construct according to Example 1, the stability of cells using live-dead staining (LIVE/DEAD Viability/Cytotoxicity kit, Invitrogen, USA) and the change in cell proliferation ability using an EZ-Cytox assay kit (DAEILLAB Co, Korea, http://www.dacillab.co.kr) were confirmed.

As a result, as illustrated in FIGS. 2A to 2D, it was confirmed that the stability and proliferation ability of cells in a construct including human nasal turbinate-derived mesenchymal stem cell (hTMSC) were higher than those in a 3D printed construct using human bone marrow-derived mesenchymal stem cells (hBM-MSC). However, in the case of 2D culture, it was confirmed that there was no big difference in stability and proliferation ability of cells for 14 days.

Example 3. Analysis of In Vitro Osteo-Differentiation Ability of 3D Printed Stem Cell Construct After a 3D bioprinted construct was fabricated according to Example 1, put into a culture broth supplemented with 10% or 20% FBS and stabilized for one day, the next day, the culture broth was exchanged with a culture broth for osteo-differentiation (DMEM supplemented with 10% FBS, 100 U/ml penicillin, 100 mg/ml streptomycin, 0.1 mM dexamethasone, 50 mM ascorbate-2-phosphate, and 10 mM beta-glycerol iron phosphate), and then the 3D bioprinted construct was cultured for 3 weeks while exchanging the media once every two to three days.

After the culture was completed, the resulting product was washed three times with 1×PBS and fixed with 2% paraformaldehyde for 20 minutes, and then washed three times with deionized water. Thereafter, the product was allowed to react in a 2% alizarin red solution for 30 minutes and washed three times with deionized water, and then the calcium accumulation was analyzed by a general optical microscope.

Further, after the culture was completed, the resulting product was washed three times with 1×PBS and fixed with 2% paraformaldehyde for 20 minutes, and then washed three times with PBS. Permeabilization (a cell membrane was perforated for staining.) was performed using 0.1% Triton X-100, and after the resulting product was washed with PBS, nonspecific binding was blocked by treatment with a 1% normal goat serum at room temperature for 1 hour, and then after treatment with a primary antibody against an osteo-differentiation-related protein (Runt-related transcription factor: RUNX2, osteocalcin: OCN) and a reaction was carried out at 4° C. for 24 hours, the resulting product was cleaned with PBS, treated with a secondary antibody (Alexa Fluor 594-conjugate or 488-conjugate) with fluorescence against the primary antibody, and allowed to react at room temperature for 1 hour. After the reactant was cleaned with PBS and mounted with a mounting solution, it was analyzed by immunofluorescence staining whether the osteo-differentiation-related protein was expressed using confocal microscopy. DAPI refers to 4',6-diamidino-2-phenylindole for counter staining.

Figure 3A:
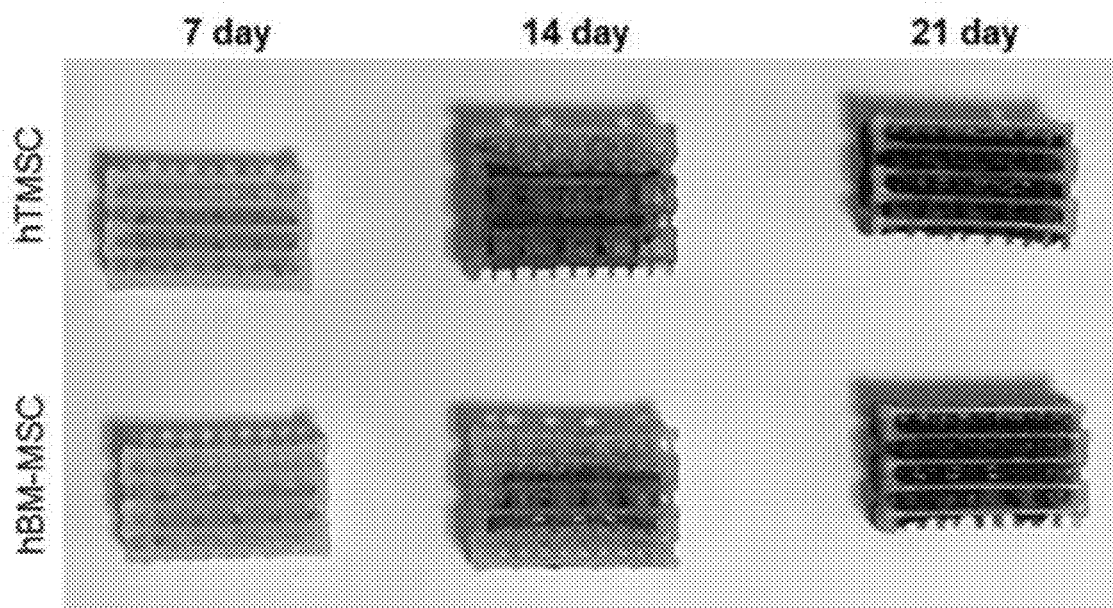
FIG. 3A is a view illustrating resulting products that induce 3D bioprinted constructs to osteo-differentiation in a culture broth for osteo-differentiation for 1 to 3 weeks.

As a result, as illustrated in FIG. 3A, it could be confirmed that at week 2 and week 3 of differentiation through staining with an alizarin red solution, osteo-differentiation was better achieved in a construct including human nasal turbinate-derived mesenchymal stem cells than in a 3D bioprinted construct using bone marrow-derived mesenchymal stem cells.

Figure 3B:
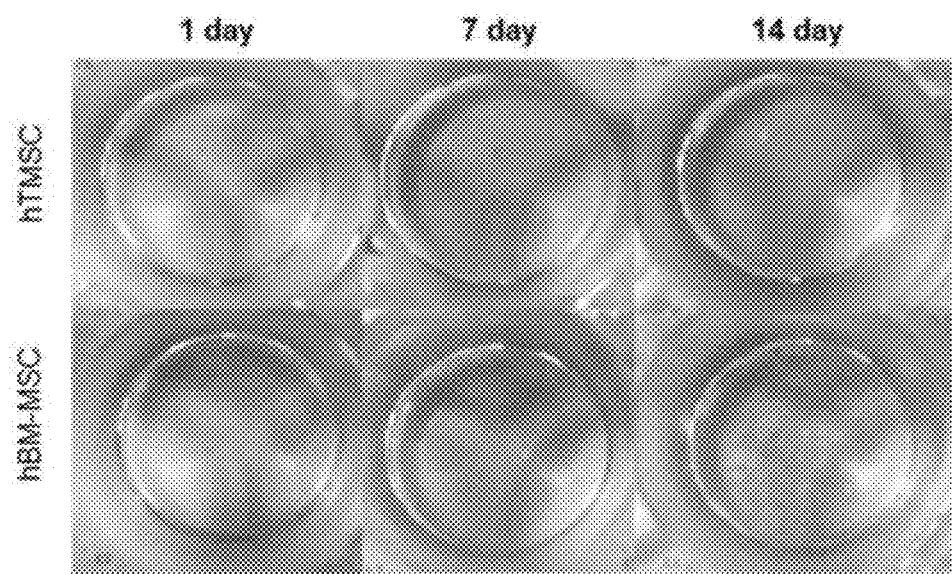
FIG. 3B is a view illustrating the results of observing calcium accumulation in a 3D bioprinted construct in which osteo-differentiation has been induced using a general optical microscope.

However, as illustrated in FIG. 3B, in the case of 2D culture, no big difference in differentiation ability between the two cell groups was observed.

Figure 3C:
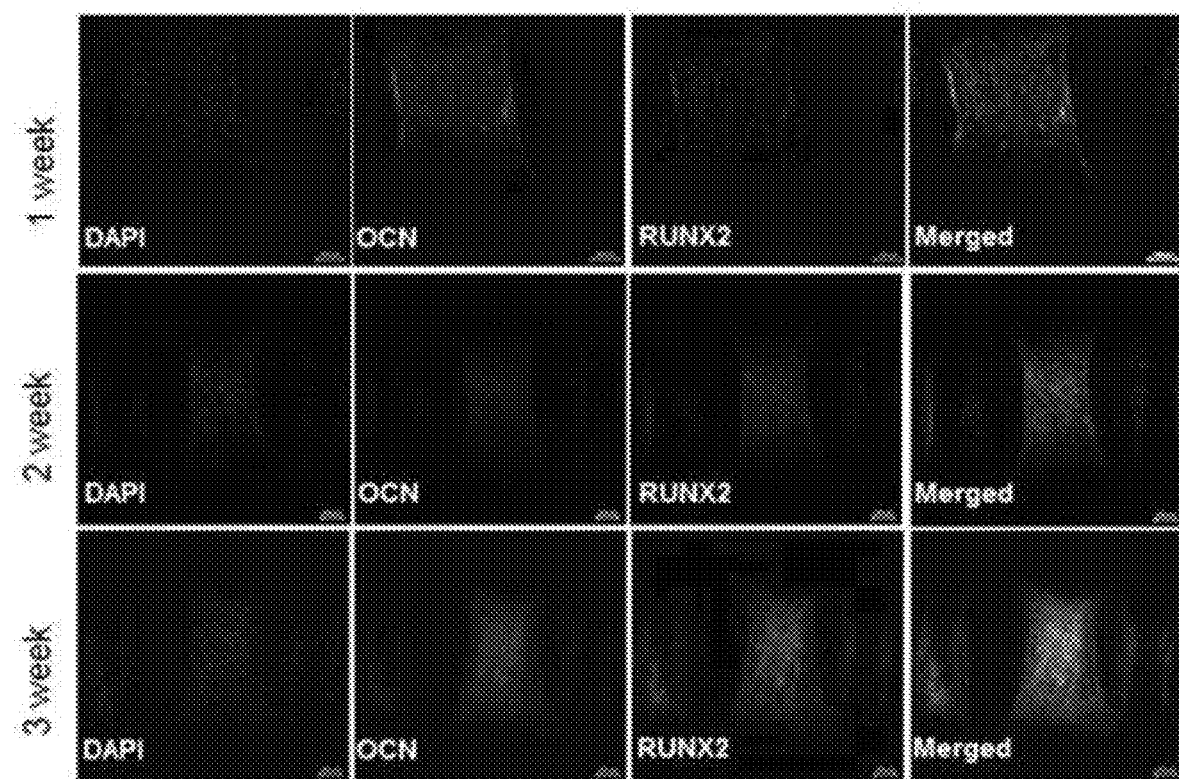
FIG. 3C is a view illustrating the results of analyzing whether an osteo-differentiation-related protein (RUNX2) is expressed in a 3D bioprinted construct including human nasal turbinate-derived mesenchymal stem cells in which osteo-differentiation has been induced by immunofluorescence staining.
Figure 3D:
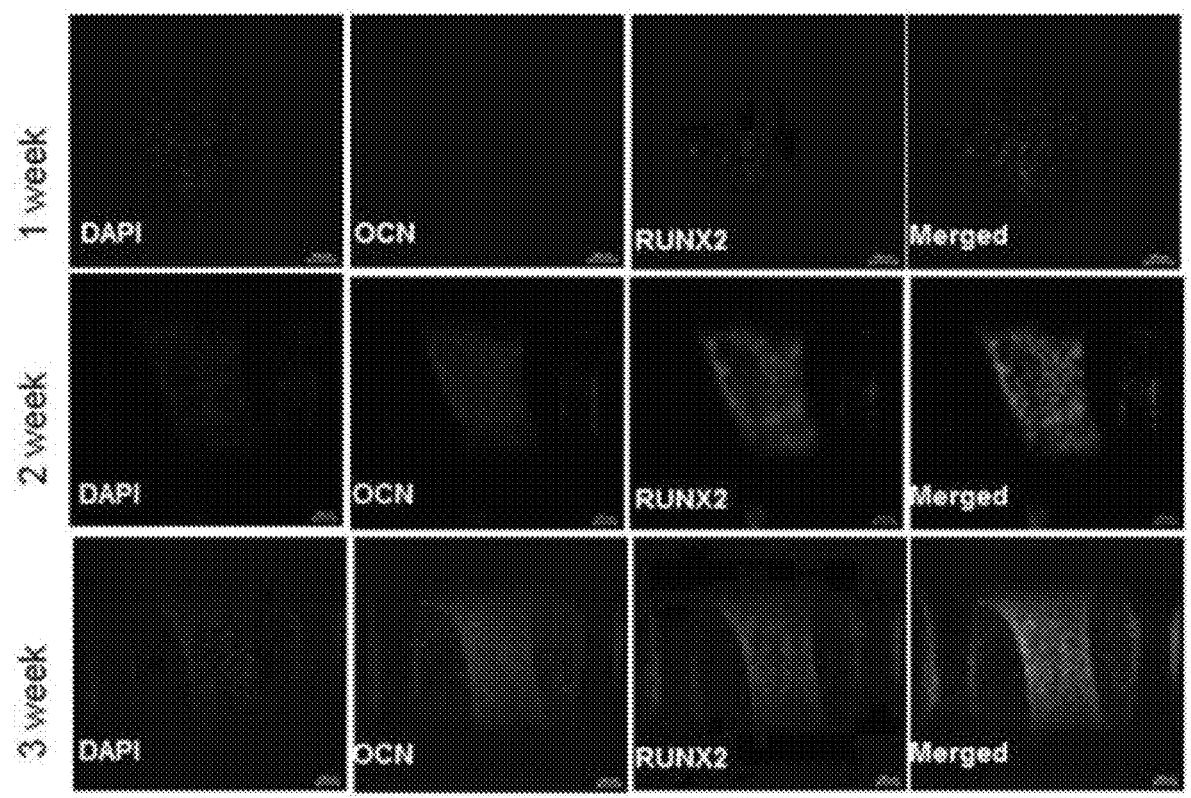
FIG. 3D is a view illustrating the results of analyzing whether an osteo-differentiation-related protein (RUNX2) is expressed in a 3D bioprinted construct including human bone marrow-derived mesenchymal stem cells in which osteo-differentiation has been induced by immunofluorescence staining.

In addition, as illustrated in FIGS. 3C and 3D, it was confirmed that at week 3 of differentiation, the RUNX2 protein was expressed more strongly in a construct including nasal turbinate-derived mesenchymal stem cells than in a 3D bioprinted construct using bone marrow-derived mesenchymal stem cells.

Example 4. Analysis of In Vivo Survival and Osteo-Differentiation Ability of 3D Printed Stem Cell Construct After a 3D bioprinted construct was fabricated according to Example 1, the 3D bioprinted construct was put into a culture broth supplemented with 10% or 20% FBS and stabilized for 7 days, or osteo-differentiation was induced, and then the construct was implanted into a dorsal subcutaneous part of a balb/c nude mouse, the construct was extracted after sacrificing the animal at week 2 and week 6 after the implantation, and the cell attachment and an osteogenesis-related change (mineralized bone matrix) were observed through H&E staining (see FIGS. 4A and 4C) and MT staining (see FIGS. 4B and 4D).

A construct was obtained from the mouse, fixed with 4% paraformaldehyde, and washed with PBS the next day. After a block was created by embedding the construct in paraffin and sectioned to a thickness of 4 to 5 μm for a deparaffinization process, the paraffin section subjected to a deparaffinization process for H&E staining and Masson's trichrome (MT) staining was retrieved using proteinase K, and then washed three times with deionized water, and then permeabilization was performed using 0.3% Triton X-100, and after the resulting product was washed three times with PBS, nonspecific binding was blocked by treatment with a 1% normal goat serum at room temperature for 1 hour, and then after treatment with a primary antibody against an osteo-differentiation-related protein RUNX2 and a human nuclei marker (hNU) and a reaction was carried out at 4° C. for 24 hours, the resulting product was cleaned with PBS, treated with a secondary antibody (Alexa Fluor 594-conjugate or 488-conjugate) with fluorescence against the primary antibody, and allowed to react at room temperature for 1 hour. After the reactant was cleaned with PBS and mounted with a mounting solution, the survival and the occurrence of osteo-differentiation in the implanted cells were analyzed by immunofluorescence staining using confocal microscopy. DAPI refers to 4',6-diamidino-2-phenylindole for counter staining.

Figure 4A:
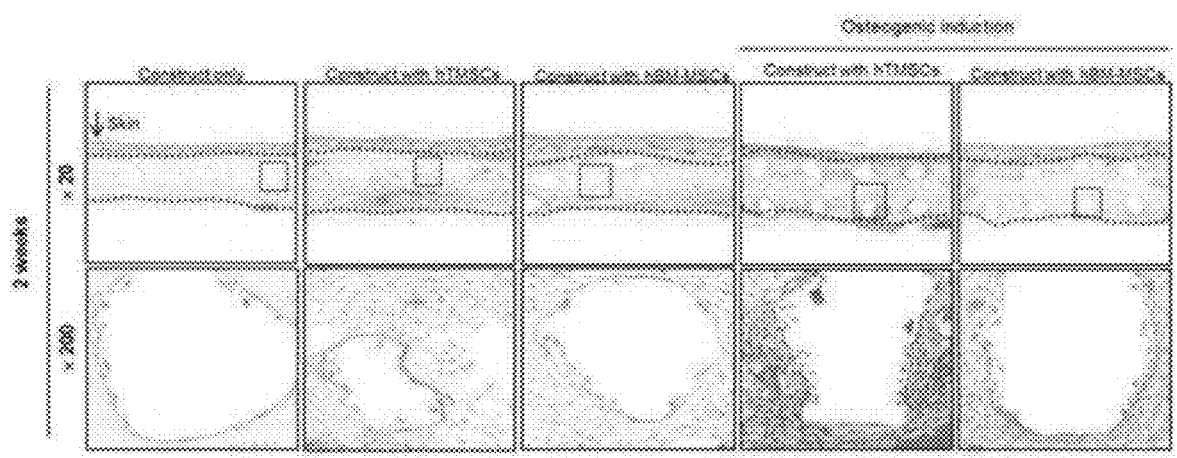
FIGS. 4A and 4C are views illustrating the results of analyzing whether cells are attached in vivo to a 3D bioprinted construct and a 3D bioprinted construct in which osteo-differentiation has been induced by immunofluorescence staining.
Figure 4B:
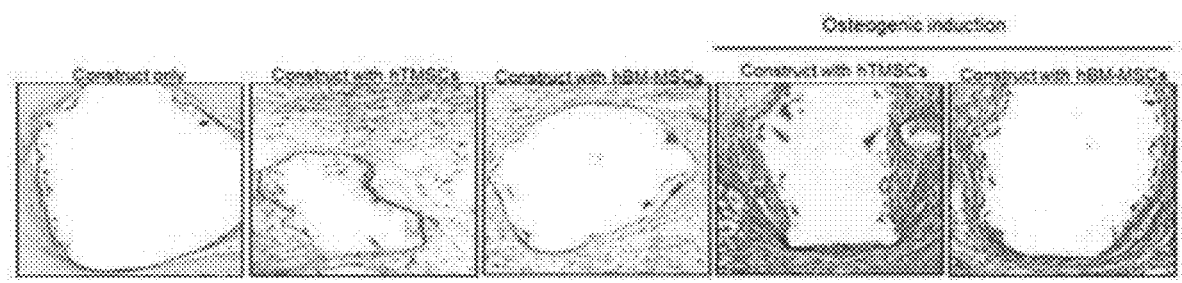
FIGS. 4B and 4D are views illustrating the results of analyzing the in vivo osteogenic differentiation ability of a 3D bioprinted construct and a 3D bioprinted construct in which osteo-differentiation has been induced by immunofluorescence staining.
Figure 4C:
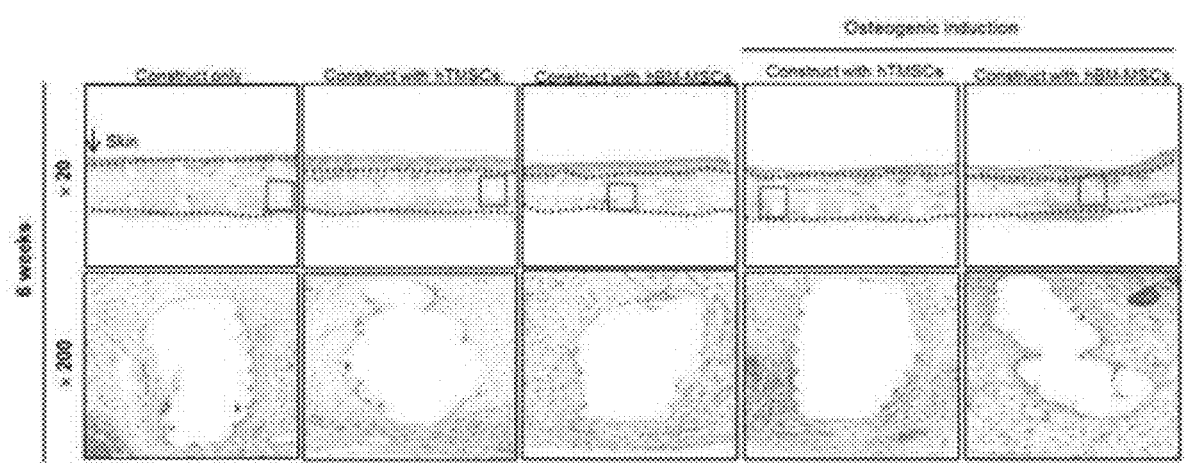

As a result, as illustrated in FIGS. 4A and 4C, it was confirmed through H&E staining that in the group in which the 3D bioprinted construct was implanted, cells were well adhered in vivo 2 weeks later, and it was confirmed that in cells from the human nasal turbinate-derived mesenchymal stem cell-based 3D bioprinted construct group and from the group in which the osteo-differentiation was induced in vitro for 7 days, in vivo attachment occurred more remarkably than in the bone marrow-derived mesenchymal stem cells.

Figure 4D:
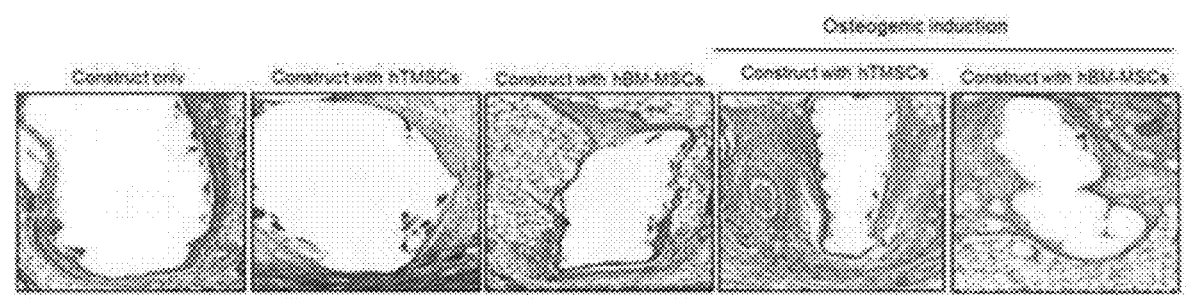

Further, as illustrated in FIGS. 4B and 4D, it was confirmed through H&E staining and MT staining that in the human nasal turbinate-derived mesenchymal stem cell-based 3D bioprinted construct in which osteo-differentiation was induced in vitro for 3 days, the possibility of in vivo osteo-differentiation and calcium accumulation was much higher. In addition, as illustrated in FIG. 4E, it was confirmed that even after 6 weeks, calcium accumulation was more obviously shown in the group in which the human nasal turbinate-derived mesenchymal stem cell-based 3D bioprinted construct in which osteo-differentiation was induced was implanted.

Figure 4E:
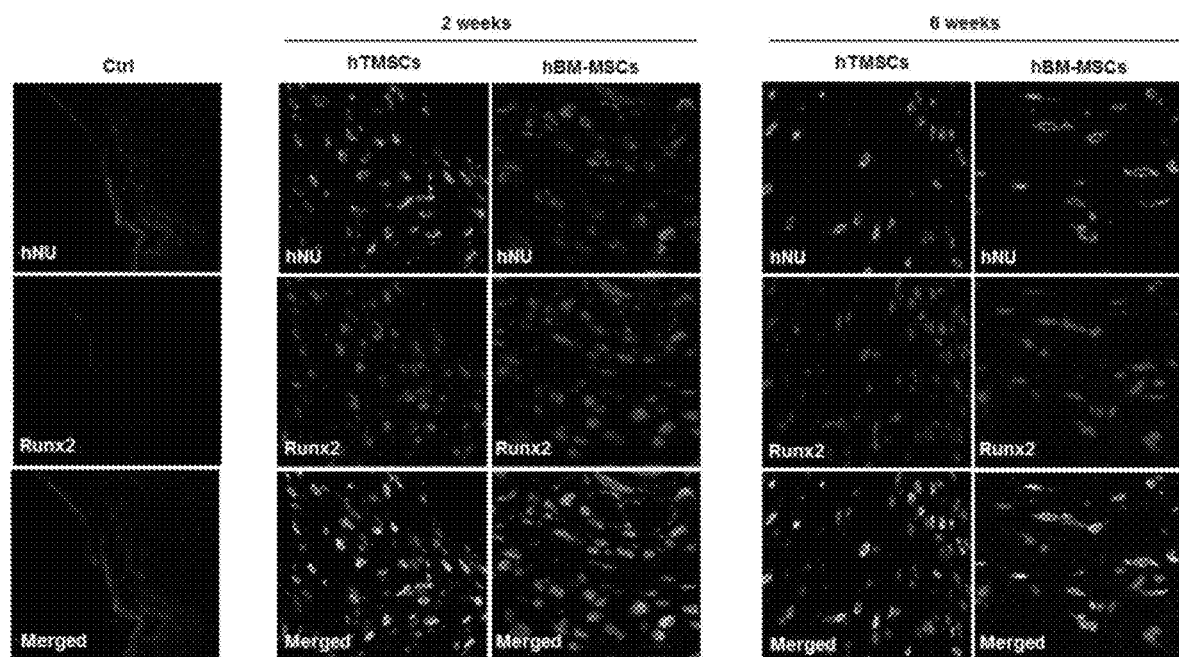
FIG. 4E is a view illustrating the results of analyzing whether cells are attached in vivo to a 3D bioprinted construct in which osteo-differentiation has been induced by immunofluorescence staining against human nuclei.

In addition, as illustrated in FIG. 4E, as a result of immunofluorescence staining against human nuclei, it was confirmed that cells were well attached in the group in which the human nasal turbinate-derived mesenchymal stem cell-based 3D bioprinted construct in which osteo-differentiation was induced in vitro for 7 days was implanted, and as a result of RUX2 immunostaining, it was confirmed that better differentiation into osteocytes occurred.

Figure 5A:
FIG. 5A is a view illustrating that a nasal turbinate-derived or bone marrow-derived mesenchymal stem cell-based 3D bioprinted construct is implanted into a tibial defect model.
Figure 5B:
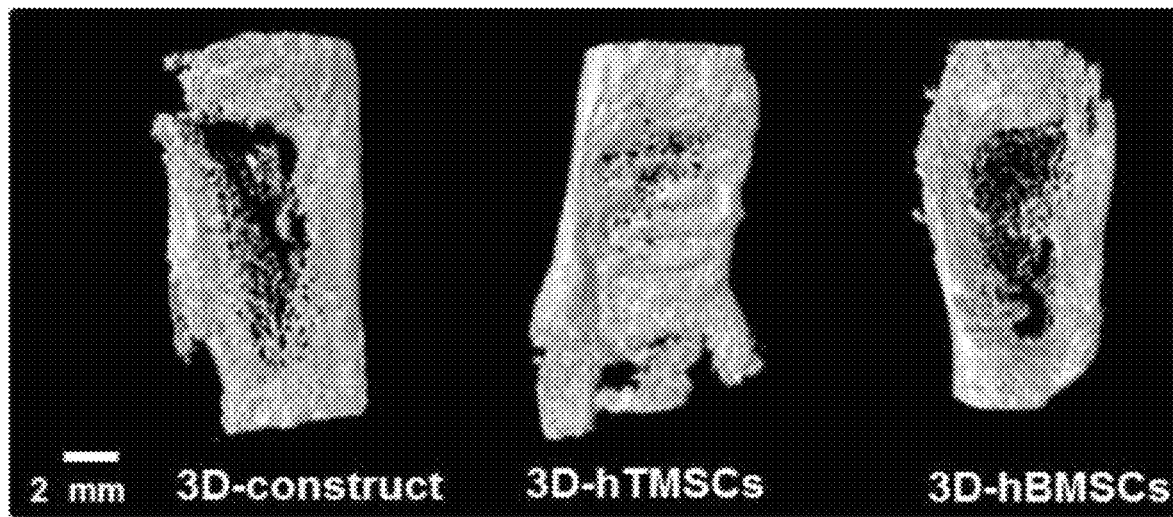
FIG. 5B is a view illustrating the degrees of osteo-regeneration by fixing iliac tissues extracted after sacrifice of an animal with 4% paraformaldehyde, and using micro-computed tomography (micro-CT) to compare a 3D construct with a mesenchymal stem cell-based 3D bioprinted construct.
Figure 5C:
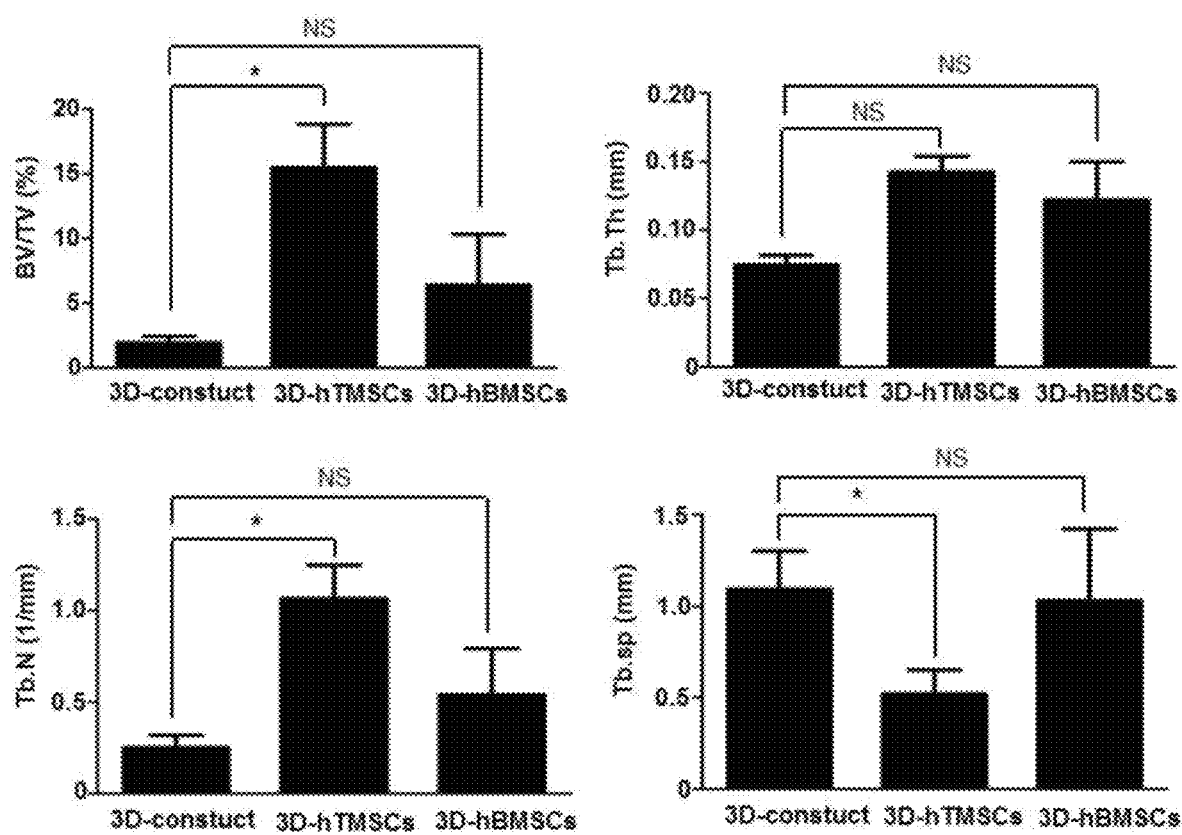
FIG. 5C is a set of views illustrating the results of measuring and analyzing the degrees of osteo-regeneration in bone defect sites into which a nasal turbinate-derived mesenchymal stem cell-based 3D bioprinted construct and a 3D construct have been implanted, based on the tissue volume (BV/TV) within the defect area, the trabecular number (Tb.N.), the trabecular thickness (Tb.Th.), and the trabecular separation (Tb.Sp.), using micro-computed tomography (micro-CT).

Example 5. Analysis of In Vivo Bone Defect Regeneration Ability of 3D Printed Stem Cell Construct After a 3D bioprinted construct was fabricated according to Example 1, bone differentiation was induced by putting the construct in a culture broth for 7 days, and then the construct was implanted into ilium defect parts of Sprague-Dawley rats, and the constructs were extracted by sacrificing the animals two weeks and five weeks later. The construct was fixed with 4% paraformaldehyde, and the degrees of osteo-regeneration were measured and analyzed based on the tissue volume (BV/TV) within the defect area, the trabecular number (Tb.N.), the trabecular thickness (Tb.Th.), and the trabecular separation (Tb.Sp.), using micro-computed tomography (micro-CT) (FIGS. 5B and 5C). As a result, as illustrated in FIGS. 5B and 5C, through micro-CT analysis, it was confirmed that two weeks later, the regeneration of bone defect parts occurred in the group in which the 3D bioprinted construct had been implanted in comparison with the group in which a cell-free 3D construct had been implanted, and it was confirmed that the osteo-regeneration occurred more remarkably in the human nasal turbinate-derived mesenchymal stem cell-based 3D bioprinted construct group than in the bone marrow-derived mesenchymal stem cell-based 3D bioprinted construct group, and thus, the size of a defect was reduced.

Example 6. Analysis of Survival and Differentiation Ability in Bone Defect Site of 3D Printed Stem Cell Construct After the micro-CT analysis was completed, an osteogenesis-related change (mineralized bone matrix) was observed in the construct through H&E staining (see FIGS. 4A and 4C) and through Masson's trichrome (MT) staining (see FIGS. 4B and 4D).

After a block was created by embedding the construct fixed with 4% paraformaldehyde in paraffin and sectioned to a thickness of 4 to 5 μm for a deparaffinization process, H&E staining and MT staining were performed. Further, in order to see the expression of an osteo-differentiation-related protein RUNX2 and a human nuclei marker (hNU), the paraffin section subjected to deparaffinization process was retrieved using proteinase K, and then washed three times with deionized water, and then permeabilization was performed using 0.3% Triton X-100, and after the resulting product was washed three times with PBS, nonspecific binding was blocked by treatment with a 1% normal goat serum at room temperature for 1 hour, and then after treatment with a primary antibody against RUNX2 and a human nuclei marker (hNU) and an reaction was carried out at 4° ° C. for 24 hours, the resulting product was cleaned with PBS, treated with a secondary antibody (Alexa Fluor 594-conjugate or 488-conjugate) with fluorescence against the primary antibody, and allowed to react at room temperature for 1 hour. After the reactant was cleaned with PBS and mounted with a mounting solution, the survival and the occurrence of osteo-differentiation in the implanted cells were analyzed by immunofluorescence staining using confocal microscopy. DAPI refers to 4',6-diamidino-2-phenylindole for counter staining.

Figure 6A:
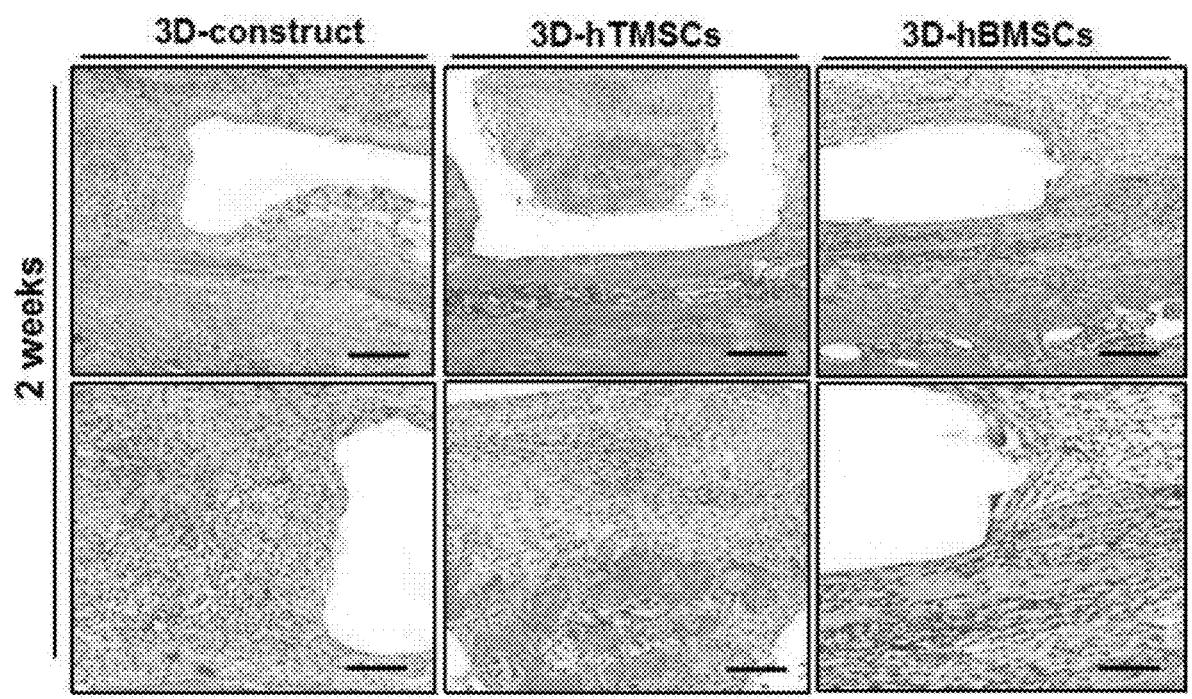
FIG. 6A is a view illustrating the results of confirming through H&E staining that osteo-regeneration appears 2 weeks later in a group in which a 3D bioprinted construct has been implanted.
Figure 6B:
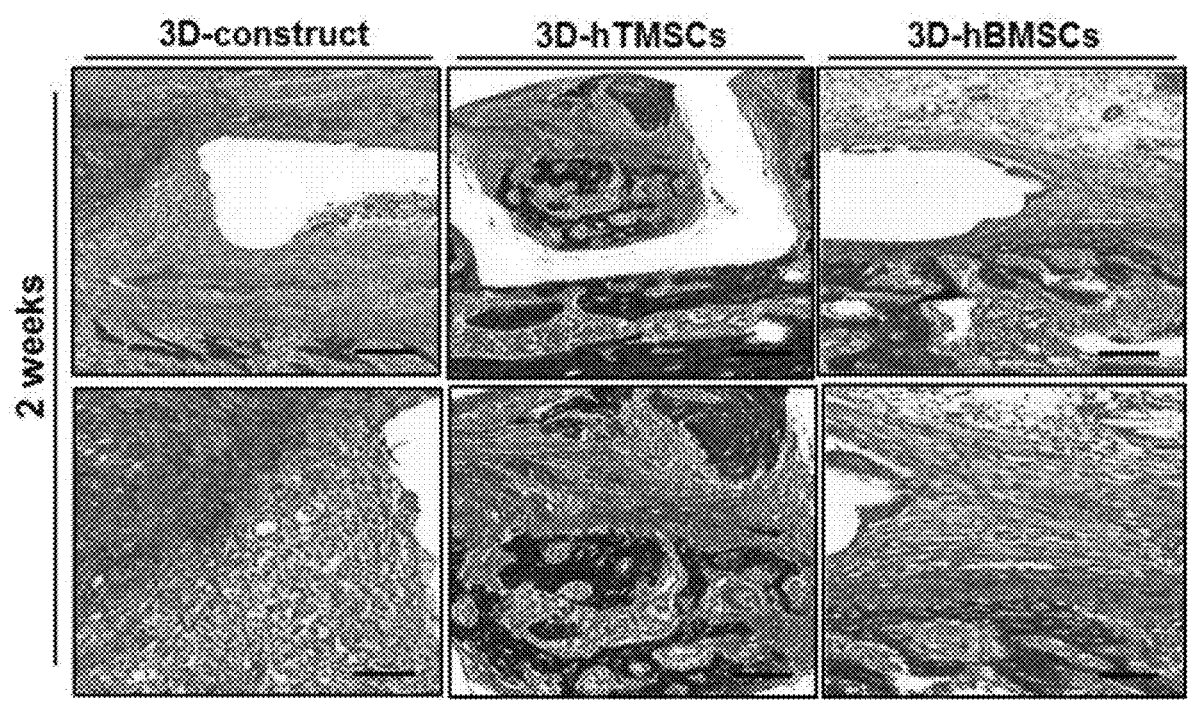
FIG. 6B is a view illustrating the results of observing in vivo osteo-differentiation and calcium accumulation in nasal turbinate-derived mesenchymal stem cell-based 3D bioprinted constructs through Masson's trichrome (MT) staining.

As a result, as illustrated in FIG. 6A, a part appearing to be dark red in color was confirmed more frequently in the group in which the nasal turbinate-derived mesenchymal stem cell-based 3D bioprinted construct had been implanted than in the group in which the bone marrow-based mesenchymal stem cell-based 3D bioprinted construct had been implanted, and thus, it was confirmed that two weeks later, the osteo-regeneration was better induced in the group in which the human nasal turbinate-derived mesenchymal stem cell-based 3D bioprinted construct had been implanted than in the group in which the bone marrow-derived mesenchymal stem cell-based 3D bioprinted construct had been implanted, and as illustrated in FIG. 6B, it was confirmed through MT staining that the possibility of in vivo osteo-differentiation and calcium accumulation was higher when the human nasal turbinate-derived mesenchymal stem cell-based 3D bioprinted construct was implanted than that when bone marrow-derived mesenchymal stem cells were implanted.

Figure 6C:
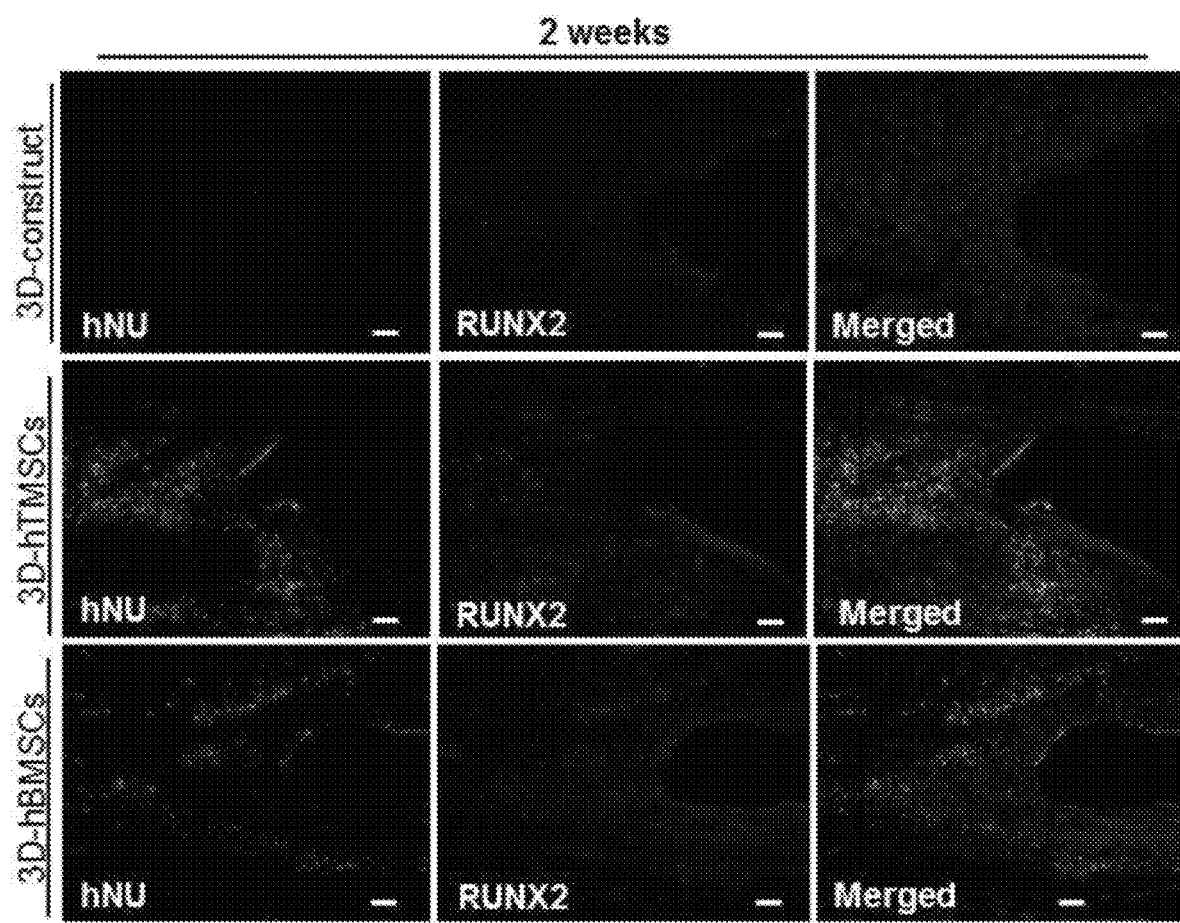
FIGS. 6C and 6D are views illustrating the results of confirming whether cells are attached in groups in which nasal turbinate-derived mesenchymal stem cell- and bone marrow-derived mesenchymal stem cell-based 3D bioprinted constructs have been implanted and whether cells are differentiated into osteocytes by immunofluorescence for RUNX2 and human nuclei.
Figure 6D:
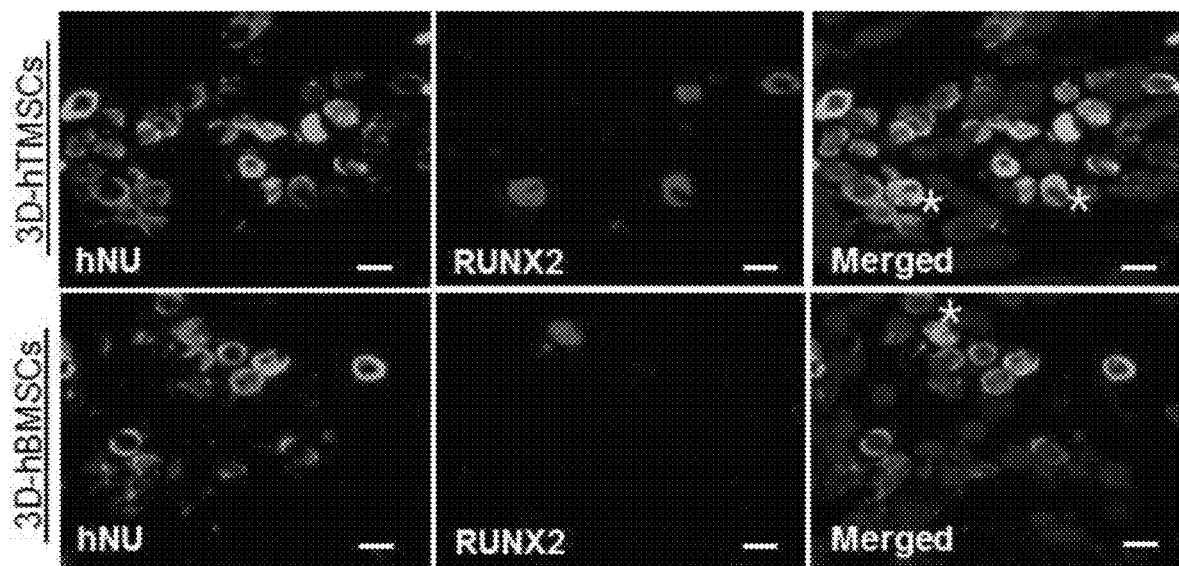
Figure 6E:
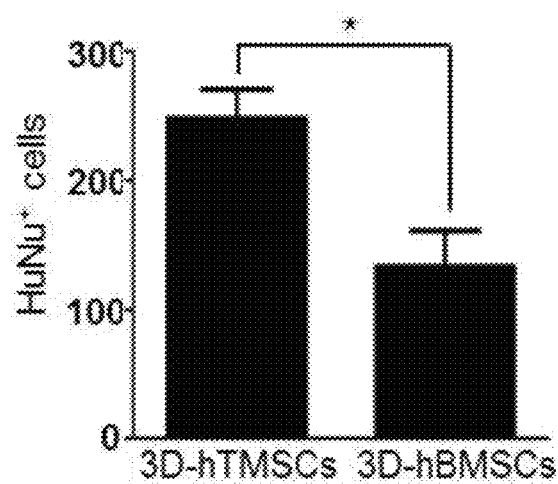
FIG. 6E is a view illustrating the results of confirming the number of human nuclei cells shown by immunofluorescence for human nuclei in order to confirm whether cells are attached in groups in which human nasal turbinate and bone marrow-derived mesenchymal stem cell-based 3D bioprinted constructs have been implanted and whether cells are differentiated into osteocytes.

In addition, as illustrated in FIGS. 6C, 6D, and 6E, as a result of immunofluorescence staining against RUNX2 and human nuclei, it was confirmed that cells were better attached in the group in which the nasal turbinate-derived mesenchymal stem cell-based 3D bioprinted construct had been implanted than in the group in which the bone marrow-based mesenchymal stem cell-based 3D bioprinted construct had been implanted, and as a result of RUNX2 immunostaining, it was confirmed that differentiation of the implanted stem cells into osteocytes more frequently occurred in the group in which the human nasal turbinate-derived mesenchymal stem cell-based 3D bioprinted construct had been implanted than in the group in which the bone marrow-based mesenchymal stem cell-based 3D bioprinted construct had been implanted.

The above-described description of the present invention is provided for illustrative purposes, and a person skilled in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

The present invention relates to a method for fabricating a human nasal turbinate-derived mesenchymal stem cell-based 3D bioprinted construct and a use thereof, and through the present invention, nasal turbinate-derived mesenchymal stem cells allow the easy fabrication of 3D bioprinted constructs which are thus expected to make a great contribution to the practical use of cellular therapeutic agents. In addition, the 3D bioprinted construct fabricated by the method of the present invention has the same genetic origin as the used human nasal turbinate-derived mesenchymal stem cells, and thus enables an immuno-compatible cellular therapeutic agent tailored to each individual to be provided.

The invention claimed is:

1. A method for treating a bone defect comprising administering to a subject in need thereof, a cellular therapeutic agent comprising a human nasal turbinate-derived mesenchymal stem cell-based 3D bioprinted stem cell construct as an active ingredient,
wherein the human nasal turbinate-derived mesenchymal stem cell-based 3D bioprinted stem cell construct has bone defect regeneration ability, and wherein the human nasal turbinate-derived mesenchymal stem cell is differentiated into osteocytes.

2. The method of claim 1, wherein the human nasal turbinate-derived mesenchymal stem cell-based 3D bioprinted stem cell construct is fabricated by a method comprising:
   (a) isolating mesenchymal stem cells from a nasal turbinate tissue collected during the process of surgically removing the human nasal turbinate;
   (b) fabricating a bio-ink by encapsulating the isolated mesenchymal stem cells in a hydrogel; and
   (c) fabricating a 3D bioprinted stem cell construct by micro-extruding the bio-ink with polycaprolactone (PCL) using a multihead dispenser.

3. The method of claim 2, further comprising stabilizing a step of putting the 3D bioprinted stem cell construct fabricated in step (c) in a stabilization culture broth, the stabilization culture broth comprising up to 20% FBS (fetal bovine serum).

4. The method of claim 2, wherein the hydrogel in step (b) is collagen or alginate.

* * * * *